(12) United States Patent
Narayanan et al.

(10) Patent No.: US 8,747,871 B2
(45) Date of Patent: Jun. 10, 2014

(54) SYNERGISTIC MATRIX COMPOSITE FOR MAKING STABLE MICROEMULSIONS OF ACTIVE INGREDIENTS

(75) Inventors: Kolazi S. Narayanan, Wayne, NJ (US); Domingo Jon, New York, NY (US); Jayanti Patel, Elmwood Park, NJ (US); Karen Winkowski, Springfield, NJ (US); Andreas Mitschke, Memmingen (DE); Otto W. Gordon, Apples (CH)

(73) Assignee: ISP Investments Inc., Wilmington, DE (US)

( * ) Notice: Subject to any disclaimer, the term of this patent is extended or adjusted under 35 U.S.C. 154(b) by 1072 days.

(21) Appl. No.: 11/540,981

(22) Filed: Sep. 28, 2006

(65) Prior Publication Data

US 2008/0081059 A1 Apr. 3, 2008

(51) Int. Cl.
*A01N 25/00* (2006.01)
*A61K 8/37* (2006.01)

(52) U.S. Cl.
USPC .................................... 424/405; 424/70.22

(58) Field of Classification Search
CPC ....... A01N 25/04; A01N 27/00; A01N 31/08; A01N 53/00; A01N 65/00; A61Q 5/02; C09D 5/02; C11D 17/0021
USPC .............................................. 424/405, 70.22
See application file for complete search history.

(56) References Cited

U.S. PATENT DOCUMENTS

| | | | |
|---|---|---|---|
| 3,929,634 A | 12/1975 | Schuller | |
| 4,275,031 A | 6/1981 | Fischer et al. | |
| 4,713,238 A | 12/1987 | Barabas | |
| 4,943,586 A | 7/1990 | Bowers et al. | |
| 5,145,607 A | 9/1992 | Rich | |
| 5,212,213 A | 5/1993 | Hunter | |
| 5,298,529 A | 3/1994 | Narayanan | |
| 5,596,032 A | 1/1997 | Schilling et al. | |
| 5,766,635 A | 6/1998 | Spenleuhauer et al. | |
| 5,798,111 A | 8/1998 | Kanga et al. | |
| 6,045,816 A | 4/2000 | Narayanan et al. | |
| 6,183,757 B1 | 2/2001 | Beerse et al. | |
| 6,187,715 B1 * | 2/2001 | Narayanan et al. | 504/118 |
| 6,190,674 B1 | 2/2001 | Beerse et al. | |
| 6,190,675 B1 | 2/2001 | Beerse et al. | |
| 6,214,363 B1 | 4/2001 | Beerse et al. | |
| 6,242,398 B1 | 6/2001 | Chambers et al. | |
| 6,251,416 B1 | 6/2001 | Narayanan et al. | |
| 6,346,273 B1 | 2/2002 | Saettone et al. | |
| 6,365,146 B1 | 4/2002 | Uhrich | |
| 6,413,921 B1 | 7/2002 | Childers et al. | |
| 6,451,339 B2 | 9/2002 | Patel et al. | |
| 6,541,516 B1 * | 4/2003 | Narayanan et al. | 514/531 |
| 6,555,228 B2 * | 4/2003 | Guritza | 428/414 |
| 6,998,426 B2 | 2/2006 | L'Alloret et al. | |
| 7,008,600 B2 | 3/2006 | Katsigras et al. | |
| 7,081,450 B2 | 7/2006 | Goldshtein | |
| 7,147,873 B2 | 12/2006 | Scholz et al. | |
| 2004/0102345 A1 | 5/2004 | Orchowski et al. | |
| 2004/0166168 A1 * | 8/2004 | Mathiowitz et al. | 424/490 |
| 2005/0032655 A1 | 2/2005 | Jurek et al. | |
| 2005/0058710 A1 | 3/2005 | Straub et al. | |
| 2006/0045914 A1 | 3/2006 | Narayanan et al. | |
| 2006/0079421 A1 | 4/2006 | Wagner et al. | |
| 2006/0134036 A1 * | 6/2006 | Scancarella et al. | 424/65 |
| 2007/0020201 A1 | 1/2007 | Boyd et al. | |
| 2007/0224135 A1 | 9/2007 | Liu | |

FOREIGN PATENT DOCUMENTS

| | | |
|---|---|---|
| JP | 360163805 | 8/1985 |
| WO | 2006/026174 | 3/2006 |
| WO | 2006/028649 | 3/2006 |
| WO | 2008/016837 | 2/2008 |

OTHER PUBLICATIONS

International Search Report, PCT/US2007/079665 (dated Apr. 3, 2008; published Jul. 3, 2008).
International Preliminary Report of Patentability, PCT/US2007/079665 (dated Mar. 31, 2009).
International Search Report, PCT/US2005/028681 (dated Nov. 28, 2006; published Feb. 1, 2007).
International Preliminary Report on Patentability, PCT/US2005/028681 (dated Feb. 13, 2007).
International Search Report, PCT/US2005/029340 (dated Mar. 28, 2006; published Sep. 14, 2006).
International Preliminary Report on Patentability, PCT/US2005/029340 (dated Feb. 28, 2007).
Office Action, U.S. Appl. No. 10/926,510 (Apr. 8, 2008).
Office Action, U.S. Appl. No. 10/926,510 (Sep. 8, 2008).
Final Office Action, U.S. Appl. No. 10/926,510 (Apr. 2, 2009).
Chari, K. et al., "Competitive Adsorption at the Air-Water Interface from a Self-Assembling Polymer-Surfactant Mixture," J. Phys. Chem. B, 2004, 108, pp. 11442-11446.
Nagarajan, R., "Polymer-Surfactant Interactions," New Horizons: Detergents for the New Millennium Conference Invited Papers, published by American Oil Chemists Society and Consumer Specialty Products Association, Fort Myers, Florida (20 pages) (2001).
Odeh, F., "Polymer-Surfactant Interaction" (45 pages) (Feb. 16, 2006).
Olofsson, G. et al., "Interactions between surfactants and uncharged polymers in aqueous solution studied by microcalorimetry," Pure & Appl. Chem., vol. 66, No. 3, pp. 527-532 (1994).

(Continued)

*Primary Examiner* — Janet Epps-Smith
*Assistant Examiner* — Courtney Brown
(74) *Attorney, Agent, or Firm* — Thompson Hine LLP; William J. Davis

(57) ABSTRACT

What is described herein is a synergistic matrix composite for making a stable microemulsion in water of an active ingredient comprising a first matrix composition including by wt. (a) 5-30% of a $C_8$-$C_{18}$ N-alkyl pyrrolidone, (b) optionally, 5-60% of a water insoluble organic solvent soluble therein, (c) 30-70% of a non-ionic emulsifier, and (d) 1-15% of an EO/PO/EO copolymer, and, (e) optionally, 1-5% of a surface active buffering agent, e.g. a branched alkyl ethoxylated phosphate ester, a second matrix composition comprising a polar polymeric material, e.g. polyethylene glycol, and/or a neutralized derivatized vegetable oil, e.g. maleated linseed oil, which composite is capable of loading a higher amount of said active than either composition alone.

11 Claims, No Drawings

(56) References Cited

OTHER PUBLICATIONS

"BioChemika Ultra—Detergents/Surfactants," from the web site of Sigma-Aldrich (6 pages) (date of first publication unknown).
Leroux, J-C. et al., "Water-Soluble Amphiphilic Nanocarriers—Applications in Drug Delivery," The Drug Delivery Companies Report Autumn/Winter, PharmaVentures, Ltd. (6 pages) (2002).
International Search Report, International Application No. PCT/US2007/074535 (2 pages) (dated Sep. 29, 2008; published Dec. 18, 2008).
International Preliminary Report on Patentability, International Application No. PCT/US2007/074535 (4 pages) (dated Feb. 3, 2009).
Office Action, U.S. Appl. No. 11/496,599 (10 pages) (Oct. 1, 2008).
Office Action, U.S. Appl. No. 11/496,599 (8 pages) (Apr. 29, 2009).

* cited by examiner

SYNERGISTIC MATRIX COMPOSITE FOR MAKING STABLE MICROEMULSIONS OF ACTIVE INGREDIENTS

CROSS REFERENCE TO RELATED U.S. PATENT APPLICATIONS

This application is related to co-pending U.S. patent application Ser. No. 10/926,510, filed Aug. 26, 2004 and PCT International Patent Application PCT/US2005/028681, filed Aug. 11, 2005 (International Publication No. WO 2006/028649).

BACKGROUND OF THE INVENTION

1. Field of the Invention

This invention relates to a matrix composite for forming a microemulsion of an active ingredient in water, and, more particularly, to a synergistic matrix composite of defined first and second matrix compositions for loading a higher amount of said active ingredient than either composition alone.

2. Description of the Prior Art

The art has described microemulsion concentrates for an active ingredient. See Narayanan U.S. Pat. No. 6,045,816—issued Apr. 4, 2000 "Water-Based Microemulsion of a Pyrethroid" (Microflex®); U.S. Pat. No. 6,187,715—issued Feb. 13, 2001 "Water Based Microemulsions of a Lower Alkyl Ester of Quinoxalinyl Herbicide"; Narayanan U.S. Pat. No. 6,251,416—issued Jun. 26, 2001 "Water-Based Microemulsion of a Pyrethroid" (Microflex®)—covers the concentrates; Narayanan U.S. Pat. No. 6,541,516—issued Apr. 1, 2003 "Water Miscible Emulsions of Pyrethroid Insecticides or Triazole Fungicides": extension of Microflex using hydrophobic solvents for better stability on dilution.

The co-pending U.S. patent application cross-referenced above contains a defined matrix composition which is effective in forming microemulsions of active ingredients. However, it is desired to provide new and improved synergistic matrix composites for loading higher amounts of active in a stable microemulsifiable form in water than either composition alone.

Most active ingredients, e.g. bioactive materials, are hydrophobic organic compounds with complex structures with very little water solubility. In most applications, the bioactive materials are dispersed in water. The bio-efficacy depends on how finely the bioactive materials are dispersed prior to application on the target organism. Typical formulations of bioactive materials contain either solvents with emulsifiers or polymeric dispersants and stabilizers to formulate concentrates. The concentrates upon dilution in water produce either emulsion droplets or particulate fine dispersions. It is desirable to have the particle size distribution at <2 microns for good biological efficacy. Many solvents and/or emulsifiers have several disadvantages of being either volatile, flammable, irritating, possess aquatic toxicity, and may cause environmental issues from run off.

SUMMARY OF THE INVENTION

The synergistic matrix composite for forming stable microemulsion concentrates of high amounts of an active ingredient in water comprises, by weight, a first matrix composition including
(a) 5-30% $C_8$-$C_{18}$ N-alkyl pyrrolidone,
(b) 5-60% an organic solvent which is soluble in (a), selected from the group consisting of alcohols, ethers, esters, ketones, aldehydes, aliphatic and aromatic, and cyclic hydrocarbons, naturally occurring flavoring agents, vegetable oils, flavoring agents, fragrances, and monomers, e.g. propylene carbonate, propylene glycol, reduced vinyl pyrrolidone dimer, gamma-butyrolactone, N,N-dimethyl imidazolidone, cyclohexanone and methyl ethyl ketone, benzophenone, benzyl benzoate esters of long chain carboxylic acid with greater than 4 carbon atoms or esters with an alkyl group (from the alcohol segment has more than 4 carbon atoms, alcohols having greater than six carbons, preferably which are more hydrophilic than (a), or hydrocarbon solvents for those active ingredients having high solubility, preferably more hydrophilic than (a) and with low water solubility, (c) 30-70% of a no ionic emulsifier, e.g., castor oil ethoxylate, preferably which are alkoxylated oils with an HLB between 6-18, most preferably 8-16, (d) 1-15% of an EO/PO/EO copolymer, and optional ingredients include (e) 0-5% of a surface active buffering agent, e.g., branched alkyl ethoxylated phosphoric acid to provide the desired pH on dilution in water depending on the active ingredient, and a second matrix composition including a polar polymeric material, e.g., polyethylene glycol and/or a neutralized derivatized vegetable oil, e.g., maleated linseed oil.

Suitably, the first and second matrix compositions are present in a weight ratio of 0.1:1 to 1:0.1, preferably about 1:1.

The synergistic matrix composite of the invention is made into a stable microemulsifiable concentrate when it includes (f) 1-30% of an active ingredient, or mixtures thereof.

Upon dilution with water, the concentrate forms a stable microemulsion composition of the invention.

In this invention, the active ingredient then can be delivered to a desired site by applying the stable microemulsion composition thereto.

Suitably, the active ingredient (f) is a biocide; an agricultural chemical, e.g., a fungicide, insecticide or herbicide; a disinfectant, fragrance or cleaning oil; an organic solvent; a personal care ingredient, e.g., an emollient or dye; a water-insoluble monomer, e.g., methyl methacrylate, styrene, an alkyl maleate or cinnamate; an olefinic hydrocarbon; an ester or amide; or a flavoring agent.

DETAILED DESCRIPTION OF THE INVENTION
Typical active ingredients include:

| | |
|---|---|
| 1. | Ortho phenyl phenol |
| 2. | Para Chloro meta xylenol (PCMX) |
| 3. | Para tertiary amyl phenol |
| 4. | Para chloro ortho benzyl phenol |
| 5. | Pine oil |
| 6. | Complex mixture of perfumes/fragrances |
| 7. | Mixed phenol disinfectants |
| 8. | Mixed phenol and Quats |
| 9. | Chlorhexidine |
| 10. | IPBC |
| 11. | Permethrin |
| 12. | Deltamethrin |
| 13. | Palluthrin |
| 14. | Cyfluthrin |
| 15. | TCMTB |
| 16. | Propiconazole |
| 17. | Resmethrin |
| 18. | Insecticides and fungicides and mixtures thereof. |

METHODOLOGY

A known weight of the active ingredient was dissolved in a known weight of the synergistic matrix composite with increasing quantities of the active ingredient to prepare a stable concentrate without separation. The concentrates were diluted to different levels and the stability of the diluted samples were monitored with time to screen for any separation, or visible change in physical characteristics like color, viscosity, or turbidity. Stable concentrates were then further evaluated for retention of the active ingredients via analytical techniques like GC, HPLC, or spectral analysis including diluted samples via accelerated storage. Particle size analysis of typical samples were also measured. Turbidity values were measured for those samples which were not optically clear for comparison with equivalent commercial samples.

EXAMPLES

The compositions shown below were prepared by weighing in appropriate quantities of the ingredients to make up 100 g samples in a 4-ounce stoppered bottles. The contents were dissolved using a rotary shaker over a period of 16 hours. All compositions were homogeneous at room temperature.

Stability evaluation of the samples were carried out as previously described in U.S. Pat. No. 6,045,816. The stability of the concentrates and on dilution are shown below.

Stability of Concentrates

All concentrate compositions shown herein were clear, homogeneous solutions at ambient conditions and at 50° C. and at 0° C., when stored for three weeks. All samples passed the standard freeze thaw cycle three times of alternate storage at 50° C. and 0° C. through room temperature for 24 hours at each temperature without any separation.

Stability on Dilution

Each of the concentrates shown herein were diluted with deionized water as well as 1000 ppm WHO hard water at the rates: 1/10, 1/100, and 1/1000 and any separation was noted by visual observation as a function of time during storage for 100 days at room temperature (22° C.-25° C.) and at 4° C. The results are summarized below:

All samples at the above dilutions: 1/10, 1/100, and 1/1000 when stored at ambient temperature 22-25° C. were monitored for 100 days of storage.

Following matrices were prepared, see Examples 1, 2 and 3.

EXAMPLE 1

A 100 g first matrix composition was prepared by dissolving the following ingredients in a 4-ounce stoppered bottle: 12.5 g N-octylpyrrolidone, 74.5 g castor oil ethoxylate (30 EO), 11.0 g EO/PO (PEG oil L 31) copolymer, and 2.0 g branched ethoxylated phosphate ester (9-10 EO). This composition was designated as 1M.

EXAMPLE 2

Maleated linseed oil (Bomol 4N), obtained from ISP Biochema Schwaben GmbH was used as received. This composition was designated as 2B.

EXAMPLE 3

Preparation of Matrix of Invention

The following combinations of compositions 1M and 2B from Example 1 and Example 2, respectively, were prepared by mixing the two compositions in the ratio 0:10, 1:9, 2:8, 3:7, 4:6, 5:5, 6:4, 7:3, 8:2, 9:1, and 10:0. The best overall results were obtained with a composition containing a mixture of 1M and 2B in the weight ratio of 5:5. This composition was designated as 3BM (1:1). Matrices: 1M, 2B and 3BM (1:1) were compared by evaluating the concentrates and diluted samples for stability as described in the following Tables.

EXAMPLE 4

Experiment 4.1

Parachlorometaxylenol (PCMX) was formulated in three different matrices and stability of concentrate and dilutions were observed. Results are shown in the following Tables.

PCMX was mixed with each of the matrices 1M or 2B or 3BM. The ratio included 10:90, 20:80, 30:70, 40:60 and 50:50. The solutions were observed for three days for solubility.

1) 10%, 20%, 30%, 40% and 50% PCMX in 1M were evaluated for solubility.

TABLE 1

|  | 1 | 2 | 3 | 4 | 5 |
|---|---|---|---|---|---|
| Matrix |  |  |  |  |  |
| 1M | 90% | 80% | 70% | 60% | 50% |
| PCMX | 10% | 20% | 30% | 40% | 50% |
| Total Observation | 100% | 100% | 100% | 100% | 100% |
| T = 0 hrs | Clear | Clear | Clear | Clear | Insoluble |
| T = 3 day | Clear | Clear | Clear | Clear | Insoluble |

2) 10%, 20% and 30% PCMX in 2B were evaluated for solubility.

TABLE 2

|  | 1A | 2A | 3A |
|---|---|---|---|
| Matrix |  |  |  |
| 2B | 90% | 80% | 70% |
| PCMX | 10% | 20% | 30% |
| Total Observation | 100% | 100% | 100% |
| T = 0 hrs | Clear | Clear | Insoluble |
| T = 3 day | Clear | Clear | Insoluble |

3) 10%, 20% and 30% PCMX in matrix 3 BM were evaluated for solubility.

TABLE 3

|  | 1B | 2B | 3B |
|---|---|---|---|
| Matrix [3BM] |  |  |  |
| 1M | 45% | 40% | 35% |
| 2B | 45% | 40% | 35% |
| PCMX | 10% | 20% | 30% |
| Total Observation | 100% | 100% | 100% |
| T = 0 hrs | Clear | Clear | Clear |
| T = 3 day | Clear | Clear | Clear |

Results: The concentrates were clear in
   1M up to 40%
   2B up to 20% and
   3BM up to 30%.

Experiment: 4.2 [Effects of Dilution]

The following stable concentrates were diluted at 1/10, 1/100, and 1/1000 with de-ionized water and their stability with time, when stored at room temperature, was recorded, as shown in Table 4.

20% PCMX concentrate in 1M, 2B, and 3BM
30% PCMX concentrate in 1M, and 3BM

After five days the results showed that 1/1000 diluted solution of 20% PCMX in 1M and 1/100 and 1/1000 solutions of 20% PCMX in 3BM were optically clear. Others were either cloudy or showed precipitation. As evidenced by the relative NTU values, (turbidity values were measured by HACH instrument). From samples selected, after prolonged storage (40 days) are also shown.

TABLE 4

PCMX Compositions and stability on dilution at room temperature

|  | 1M 1 | 1M 2 | 2B 3 | 3BM 4 | 3BM 5 |
|---|---|---|---|---|---|
| Matrix 1M | 80% | 70% |  | 40% | 35% |
| Matrix 2B |  |  | 80% | 40% | 35% |
| 4 chloro 3,5 dimethyl phenol (PCMX) | 20% | 30% | 20% | 20% | 30% |
| Total Dilutions | 100% | 100% | 100% | 100% | 100% |
| T = 0 hrs |  |  |  |  |  |
| 1/10 | hazy | cloudy | hazy | hazy | cloudy |
| 1/100 | clear | cloudy | clear | clear | cloudy |
| 1/1000 | clear | hazy | clear | clear | hazy |
| T = 3 day |  |  |  |  |  |
| 1/10 | ppts | ppts | ppts | hazy | ppts |
| 1/100 | hazy | ppts | ppts | clear | ppts |
| 1/1000 | clear | cloudy | cloudy | clear | ppts |
| T = 5 day |  |  |  |  |  |
| 1/10 | ppts | ppts | ppts | hazy | ppts |
| 1/100 | hazy | ppts | ppts | clear | ppts |
| 1/1000 | clear | ppts | cloudy | clear | ppts |
| T = 40 day |  |  |  |  |  |
| 1/10 | ppt | ppt | ppt | 482 NTU | ppt |
| 1/100 | 118 NTU | ppt | ppt | 212 NTU | ppt |
| 1/1000 | 10.3 NTU | ppt | ppt | 14 NTU | ppt |

The stability study of diluted samples at 20% PCMX in 3BM, 1M and 2B at ratio of 1/10, 0.5/10, 0.25/10, 0.1/10, 0.05/10 and 0.025/10 in water were performed as follows.

Experiment: 4.3 [Freeze Thaw Stability PCMX Concentrates]

The following concentrates passed the three cycles of freeze-thaw stability evaluation.
20% PCMX concentrate in 3BM
20% PCMX concentrate in 1M
5% PCMX concentrate in 2B All concentrates were stable at room temperature on prolonged storage for more than 6 months. All samples passed three cycles of freeze-thaw stability at 50° C.-25° C.-2° C. cycles. Samples stored at 50° C. for 3 weeks and stored at 2° C. for 3 weeks and brought back to ambient conditions remained homogeneous and showed no change in physical properties.

The above 3 concentrates were diluted serially in water at 1/10, 0.5/10, 0.25/10, 0.1/10, 0.05/10 and 0.025/10. These diluted samples were stored at 2° C., 50° C. and room temperature. Clarity of the samples and any changes observed during the storage cycle are shown in Tables 5 through 10.

Table 5: Storage stability as a function of temperature.

TABLE 5

Stability of 20% PCMX in Matrix 3BM

| Ingredients | % |
|---|---|
| Matrix 2B | 40.00 |
| Matrix 1M | 40.00 |
| 4-Chloro-3,5-dimethylphenol | 20.00 |

Time: 0-180 days: Clear

20% PCMX in Matrix 3BM stored at 50° C. for 3 weeks showed no change in PCMX concentration measured via GC analysis.

| dilution in water |  |
|---|---|
| 1/10 | 2.0% |
| 0.5/10 | 1.0% |
| 0.25/10 | 0.50% |
| 0.1/10 | 0.20% |
| 0.05/10 | 0.10% |
| 0.025/10 | 0.05% |

TABLE 6

|  | 2.0% | 1.0% | 0.50% | 0.20% | 0.10% | 0.05% |
|---|---|---|---|---|---|---|
| Room Temp |  |  |  |  |  |  |
| day = 0 (Aug. 22, 2005) | cloudy | Hazy | hazy | clear | clear | clear |
| day = 1 | cloudy | Hazy | hazy | clear | clear | clear |
| day = 2 | cloudy | Hazy | hazy | clear | clear | clear |
| day = 3 (Aug. 26, 2005) | cloudy | Hazy | hazy | clear | clear | clear |
| day = 5 (Aug. 30, 2005) | cloudy | Hazy | hazy | clear | clear | clear |
| day = 7 (Sep. 1, 2005) | cloudy | hazy | hazy | clear | clear | clear |
| day = 15 | cloudy | hazy | hazy | clear | clear | clear |
| 50° C. |  |  |  |  |  |  |
| day = 1 | cloudy | hazy | slight hazy | clear | clear | clear |
| day = 2 | cloudy | hazy | slight hazy | clear | clear | clear |
| day = 3 | cloudy | hazy | slight hazy | clear | clear | clear |
| day = 5 | cloudy | hazy | slight hazy | clear | clear | clear |
| day = 7 | cloudy | hazy | slight hazy | clear | clear | clear |
| day = 15 | cloudy | hazy | slight hazy | clear | clear | clear |
| 2° C. |  |  |  |  |  |  |
| day = 1 | cloudy | hazy | hazy | clear | clear | clear |
| day = 2 | cloudy | hazy | hazy | clear | clear | clear |
| day = 3 | cloudy | hazy | hazy | clear | clear | clear |
| day = 5 | cloudy | hazy | hazy | clear | clear | clear |
| day = 7 | cloudy | hazy | hazy | clear | clear | clear |
| day = 15 | cloudy | hazy | hazy | clear | clear | clear |
| 2° C./50° C. (freeze/thaw) |  |  |  |  |  |  |
| cycle = 1 | cloudy | hazy | slight hazy | clear | clear | clear |
| cycle = 2 | cloudy | hazy | slight hazy | clear | clear | clear |
| cycle = 3 | cloudy | hazy | slight hazy | clear | clear | clear |
| cycle = 5 | cloudy | hazy | slight hazy | clear | clear | clear |
| cycle = 7 | cloudy | hazy | slight hazy | clear | clear | clear |
| cycle = 9 | cloudy | hazy | slight hazy | clear | clear | clear |

Results:
Stability study of 20% PCMX Concentrate in matrix 3BM diluted at the ratio of 1:10, 0.5:10, 0.25:10, 0.1:10, 0.05:10 and 0.025:10 were performed at 1) room temp, 2) 50° C., 3) 2° C. and 4) freeze/thaw cycles for 15 days.
  a. Below 0.1:10 dilutions all samples tested were clear at all temperature and freeze/thaw cycles for 15 days.
  b. Between 1:10 and 0.25:10 dilutions the samples were either cloudy or hazy, but no precipitation was observed.
  c. The 20% concentrate at 1/100 dilution was evaluated after storage at 50° C. for 45 days by analyzing aliquot samples via GC analysis. Samples analyzed at different time from zero, 4, 7, 15, 21, 30, and 45 days storage at 50° C. were found to contain ~0.2% PCMX, showing quantitative recovery of the active ingredient.

Results:
Stability study of 20% PCMX concentrate in 1M and dilutions at the ratio of 1:10, 0.5:10, 0.25:10, 0.1:10, 0.05:10 and 0.025:10 were performed at 1) room temp, 2) 50° C. 3) 2° C. and 4) freeze/thaw cycles for 15 days.

Below 0.025:10 dilutions all samples tested were clear at all temperature and freeze/thaw cycles for 15 days.

Between 1:10 and 0.05:10 dilutions the samples were either separated, precipitated, cloudy or hazy.

TABLE 7

Stability of 20% PCMX in Matrix 1M

| Ingredients | % |
| --- | --- |
| Matrix 1M | 80.00 |
| 4-Chloro-3,5-dimethylphenol (PCMX) | 20.00 |
| Time = 0 | Clear |
| Room Temperature | |

| dilution in water | % 4-Chloro-3,5-dimethyl-phenol |
| --- | --- |
| 1/10 | 2.0% |
| 0.5/10 | 1.0% |
| 0.25/10 | 0.50% |
| 0.1/10 | 0.20% |
| 0.05/10 | 0.10% |
| 0.025/10 | 0.05% |

TABLE 8

| | % 4-chloro 3,5-dimethyl phenol in dilutions | | | | | |
| --- | --- | --- | --- | --- | --- | --- |
| | 2.0% | 1.0% | 0.50% | 0.20% | 0.10% | 0.05% |
| Room Temp | | | | | | |
| day = 0 (Aug. 22, 2005) | cloudy | cloudy | hazy | Hazy | hazy | clear |
| day = 1 | cloudy | cloudy | hazy | Hazy | hazy | clear |
| day = 2 | cloudy | cloudy | hazy | Hazy | hazy | clear |
| day = 3 (Aug. 26, 2005) | cloudy | cloudy | hazy | Hazy | hazy | clear |
| day = 5 (Aug. 30, 2005) | ppt | cloudy | hazy | Hazy | hazy | clear |
| day = 7 (Sep. 1, 2005) | ppt | ppt | ppt | Ppt | ppt | clear |
| day = 15 | ppt | ppt | ppt | Ppt | ppt | clear |
| 50° C. | | | | | | |
| day = 1 | cloudy | cloudy | hazy | Hazy | slight hazy | clear |
| day = 2 | cloudy | cloudy | hazy | Hazy | slight hazy | clear |
| day = 3 | cloudy | cloudy | hazy | Hazy | slight hazy | clear |
| day = 5 | cloudy | cloudy | hazy | Hazy | slight hazy | clear |
| day = 7 | ppts | cloudy | hazy | Hazy | slight hazy | clear |
| day = 15 | ppts | cloudy | hazy | Hazy | slight hazy | clear |
| 2° C. | | | | | | |
| day = 1 (8/23) | cloudy | cloudy | cloudy | Hazy | clear | clear |
| day = 2 (8/24) | cloudy | cloudy | cloudy | Hazy | clear | clear |
| day = 3 | cloudy | cloudy | cloudy | Hazy | clear | clear |
| day = 5 | cloudy | cloudy | cloudy | Hazy | clear | clear |
| day = 7 | ppts | cloudy | cloudy | Hazy | clear | clear |
| day = 15 | ppts | ppts | ppts | Hazy | clear | clear |
| 2° C./50° C.(Freeze/Thaw) | | | | | | |
| cycle = 1 | cloudy | cloudy | hazy | Hazy | clear | clear |
| cycle = 2 | cloudy | cloudy | hazy | Hazy | clear | clear |
| cycle = 3 | cloudy | cloudy | hazy | Hazy | clear | clear |
| cycle = 5 | ppts | ppts | hazy | Hazy | clear | clear |
| cycle = 7 | ppts | ppts | hazy | Hazy | clear | clear |
| cycle = 9 | ppts | ppts | Hazy | Hazy | clear | clear |

TABLE 9

Stability of 10% PCMX in Matrix 2B

| Ingredients | % |
| --- | --- |
| Matrix 2B | 90.00 |
| 4-Chloro-3,5-dimethylphenol (PCMX) | 10.00 |

TABLE 10

| | Dilution | | | | |
| --- | --- | --- | --- | --- | --- |
| | 1/5 | 1/10 | 1/20 | 1/50 | 1/100 |
| | 2.0% | 1.0% | 0.50% | 0.20% | 0.10% |
| Room Temp. Days | | | | | |
| 0 | cloudy | cloudy | cloudy | cloudy | cloudy |
| 1 | cloudy | cloudy | cloudy | cloudy | cloudy |
| 2 | cloudy | cloudy | cloudy | cloudy | cloudy |
| 5 | cloudy | cloudy | cloudy | cloudy | cloudy |

TABLE 10-continued

| | Dilution | | | | |
|---|---|---|---|---|---|
| | 1/5 2.0% | 1/10 1.0% | 1/20 0.50% | 1/50 0.20% | 1/100 0.10% |
| 7 | ppt | ppt | ppt | cloudy | cloudy |
| 15 | ppt | ppt | ppt | cloudy | cloudy |
| 45 | ppt | ppt | ppt | cloudy | cloudy |
| 50° C. | | | | | |
| 1 | cloudy | cloudy | cloudy | cloudy | cloudy |
| 2 | ppt | ppt | ppt | cloudy | cloudy |
| 5 | ppt | ppt | ppt | cloudy | cloudy |
| 7 | ppt | ppt | ppt | cloudy | cloudy |
| 15 | ppt | ppt | ppt | cloudy | cloudy |
| 45 | ppt | ppt | ppt | ppt | cloudy |
| 2° C. | | | | | |
| 1 | cloudy | cloudy | cloudy | cloudy | cloudy |
| 2 | ppt | ppt | ppt | cloudy | cloudy |
| 5 | ppt | ppt | ppt | cloudy | cloudy |
| 7 | ppt | ppt | ppt | cloudy | cloudy |
| 15 | ppt | ppt | ppt | cloudy | cloudy |
| 45 | ppt | ppt | ppt | cloudy | cloudy |
| 0° C./50° C. | | | | | |
| cycle = 1 | ppt | cloudy | cloudy | cloudy | cloudy |
| cycle = 2 | ppt | cloudy | cloudy | cloudy | cloudy |
| cycle = 3 | ppt | cloudy | cloudy | cloudy | cloudy |

Results

Effective loading of PCMX was 10% in Matrix 2B

Samples at all dilutions with PCMX at 2%-0.1% were cloudy, and samples at dilutions 1/5, 1/10, and 1/20 showed separation.

EXAMPLE 5

Orthophenylphenol (OPP) was formulated in Matrix 3BM as shown in Example 4, except PCMX was replaced with OPP.

Concentrates were made at 10%, 15%, and 20% OPP and matrix 3BM to 100%.

All concentrates were clear and passed three cycles of freeze-thaw. On dilution with water to produce OPP at 0.2%, 0.1%, 0.05% from the above concentrates produced clear dilutions from a 10% Concentrate, slightly cloudy compositions from a 15% concentrate and cloudy compositions from a 20% concentrate. OPP can be formulated in Matrix 3BM at 15% OPP affording nano-particulate distribution at use levels of ~0.1% OPP.

EXAMPLE 6

Example 5 was repeated using the following concentrate.

PCMX—6% with 2-benzyl-4-Chlorophenol—6% and Matrix 3BM—88%. This concentrate was clear and on dilution at 1/10, 1/100 was also optically clear, observed for 0-20 days.

EXAMPLE 7

Example 6 was repeated using the following concentrates.

PCMX—6% with Tertiary amyl phenol—3% and Matrix 3BM—91%. This concentrate was clear and on dilution at 1/10, 1/50, and 1/150 was also optically clear, observed for 0-20 days.

EXAMPLE 8

Example 7 was repeated using the following concentrates.

2, benzyl-4-chlorophenol—5% with 2, phenyl phenol—5% and Matrix 3BM—90%. This concentrate was clear and on dilutions at 1/10, 1/50, and 1/150 was also optically clear, observed for 0-20 days.

EXAMPLE 9

Example 7 was repeated using the following concentrates.

2, benzyl-4-chlorophenol—9% with 2, phenyl phenol—1% and Matrix 3BM—90%. This concentrate was clear and on dilution at 1/10, 1/50, and 1/150 was also optically clear, observed for 0-20 days.

EXAMPLE 10

Example 9 was repeated using the following concentrates.

2, benzyl-4-chlorophenol—1% with 2, phenyl phenol—9% and Matrix 3BM—90%. This concentrate was clear and on dilution at 1/10, 1/50, and 1/150 was also optically clear, observed for 0-20 days.

EXAMPLE 11

Example 10 was repeated using the following concentrates.

2, phenyl phenol—5% with para tertiary amyl phenol—5% and Matrix 3BM—90%. This concentrate was clear and on dilution at 1/10, 1/100, and 1/1000 was also optically clear, observed for 0-20 days.

EXAMPLE 12

Example 11 was repeated using the following concentrates.

2, phenyl phenol—1% with 2, benzyl-4-chlorophenol—9% and Matrix 3BM—90%. This concentrate was clear and on dilution at 1/10, 1/100, and 1/1000 was also optically clear, observed for 0-20 days.

EXAMPLE 13

Example 12 was repeated using the following concentrates.

2, phenyl phenol—9% with 2, benzyl-4-chlorophenol—1% and Matrix 3BM—90%. This concentrate was clear and on dilution at 1/10, 1/100, and 1/1000 was also optically clear, observed for 0-20 days.

EXAMPLE 14

Example 11 was repeated using the following concentrates.

2, phenyl phenol—1% with para tertiary amyl phenol—9% and Matrix 3BM—90%. This concentrate was clear and on dilution at 1/10, 1/100, and 1/1000 was also optically clear, observed for 0-20 days.

EXAMPLE 15

Example 11 was repeated using the following concentrates.
2, phenyl phenol—5% with para tertiary amyl phenol—5% and Matrix 3BM—90%. This concentrate was clear and on dilution at 1/10, 1/100, and 1/1000 was also optically clear, observed for 0-20 days.

EXAMPLE 16

Example 15 was repeated using the following concentrates.
2, phenyl phenol—9% with para tertiary amyl phenol—1% and Matrix 3BM—90%. This concentrate was clear and on dilution at 1/10, 1/100, and 1/1000 was also optically clear, observed for 0-20 days.

EXAMPLE 17

Example 10 was repeated using the following concentrates.
2, benzyl-4-chlorophenol—9% with para tertiary amyl phenol—1% and Matrix 3BM—90%. This concentrate was clear and on dilution at 1/10, 1/100, and 1/1000 was also optically clear, observed for 0-20 days.

EXAMPLE 18

Example 17 was repeated using the following concentrates.
2, benzyl-4-chlorophenol—5% with para tertiary amyl phenol—5% and Matrix 3BM—90%. This concentrate was clear and on dilution at 1/10, 1/100, and 1/1000 was also optically clear, observed for 0-20 days.

EXAMPLE 19

Example 17 was repeated using the following concentrates.
2, benzyl-4-chlorophenol—1% with para tertiary amyl phenol—9% and Matrix 3BM—90%. This concentrate was clear and on dilution at 1/10, 1/100, and 1/1000 was also optically clear, observed for 0-20 days.

EXAMPLE 20

Example 4 was repeated using the following concentrates.
Parachlorometaxylenol—10% with Pine oil—10% and Matrix 3BM—80%. This concentrate was clear and on dilution at 1/50 with water was slightly hazy with NTU values between 66-72 over a period of 20 days. The 5% concentrate in the presence of pine oil produced clear compositions on dilution in water at 0.1-0.25% PCMX.

EXAMPLE 21

Example 20 was repeated except 20% pine oil was used, instead of 10%. Concentrate was clear and on dilution at 1/50 with water was slightly hazy with NTU values between 200 and 210, over a period of 20 days. The 5% concentrate in the presence of pine oil produced clear compositions on dilution in water at 0.1-0.25% PCMX.

EXAMPLE 22

30% commercially available pine oil 60 or pine oil 150 was dissolved in the Matrix 3BN. The composition was clear. On dilution to 1/100 in water produced optically clear composition, which remained clear for 24 hours. The pine oil concentrate was added at 1/100 dilution to a commercial cleaning composition used for mopping the floor. The floor had pine oil fragrance remaining after cleaning.

EXAMPLE 23

Example 22 was repeated by dissolving 40% pine oil in the Matrix 3BN. The composition was clear. On dilution to 1/100 in water produced slightly hazy composition with NTU value around 200. The pine oil concentrate was added at 1/100 dilution to a commercial cleaning composition used for mopping the floor. The floor had pine oil fragrance remaining after cleaning.

EXAMPLE 24

A concentrate for D-Limonene was prepared by dissolving 20% commercially available D-Limonene in 80% Matrix 3BM to produce a clear concentrate. On dilution at 1/10, 1/100, and 1/1000 in water, produced optically clear compositions. Dilutions at 1/50, 1/100, and 1/150 produced clear compositions with NTU values around 70, 40, and 30 from zero to 15 days standing.

EXAMPLE 25

Example 24 was repeated using 30% D-Limonene in the place of 20%, and 70% matrix in the place of 80% matrix. On dilution at 1/10 in water produced an emulsion. On dilution at 1/100 in water produced slightly hazy composition.

EXAMPLE 26

Example 25 was repeated except 10 g of dihydro citral was dissolved in 90 g of Matrix 3BN. This concentrate was diluted with water and diluted solutions at: 1/10, 1/100 and 1/1000 were clear.

EXAMPLE 27

Example 26 was repeated except 10 g mild orange oil was dissolved in 90 g of Matrix 3BN. This concentrate was diluted with water at 1/10, 1/100 and 1/1000, they were clear.

Examples of Fragrances

EXAMPLE 28

5-10% of commercial samples of mixed fragrances were dissolved in 90-95% Matrix 3BM. On dilution in water, produced optically clear compositions. The concentrate was also compatible with commercial detergents.

EXAMPLE 28 A

The composition of Example 28 containing 5% commercial fragrance (mixture containing several individual fragrance components), was added to a commercial detergent composition at 4%. The fragrance loaded commercial detergent composition as above contained 0.2% commercial complex fragrance mixture and 3.8% matrix of Example 28.

The above composition was evaluated for fragrance retention after washing, rinsing and line-drying cotton and polyester swatches. The washed, rinsed, dry swatches are designated 28 AW swatches. Washing was also repeated using the same commercial detergent containing 0.2% same fragrance mixture, except the composition of Example 28 was absent. These washed, rinsed, dry swatches without the Matrix of Example 28 were designated CFD swatches (commercial fragrance-detergent washed swatches).

These swatches were left to air dry at room temperature. Swatches designated 28 AW showed fragrance in the swatches as measured by smell during the drying period, while the swatches designated CFD did not demonstrate any fragrance retention at all during the drying period.

28 AW swatches showed considerable retention of fragrance compared to CFD.

EXAMPLE 28 B

Example 28 was repeated by increasing the commercial fragrance from 5-10% to 10-50%. The fragrance was completely soluble in the matrix, and when diluted in commercial detergent matrix at 0.2% fragrance was homogeneous without any phase separation.

EXAMPLE 28 C

Film-forming polymers with substantivity to fabrics like cotton/polyester can also be added to matrices shown in Example 28, 28A, 28B to enhance deposition and retention of fragrance to the fabric.

Example with 10% Ganex 216 suspension (with 1% Easy-Sperse®) at 1-20%

1) 10% of 10% Ganex suspension in Matrix 3BM, formed 2 phase that was dispersible on shaking,
2) 20% of suspension formed a cloudy system, with no separation within 9 days, and
3) 30% suspension formed a cloudy suspension which separated, however, it was dispersible on shaking.

All three samples at 1/10 dilution with water formed a hazy solution.

Addition of 10% commercial fragrance to the 3 concentrates described above did not change the phase behavior of the concentrate.

1) Dilution of all three concentrates containing commercial fragrance with water to 0.2% fragrance produced clear solutions.
2) Dilution of commercial detergent containing the commercial fragrance concentrates as above, diluted to 0.2% fragrance were clear.

EXAMPLE 28 D

Example with Ganex 216 (an Alkylated Graft Polyvinyl Pyrrolidone with C-16 Alpha Olefin Neat 1-10%)

0.6% and 10% Ganex 216 added to Matrix 3BM formed clear concentrates. Dilution at 1/10 and 1/50 with water formed a cloudy solution for both concentration. These can be used to deliver fragrance mixtures as above.

EXAMPLE 29

5% Chlorhexidine was dissolved in the Matrix 3BM and the concentrate on dilution at 1/100, and 1/1000 produced slightly hazy to optically clear compositions.

EXAMPLE 30

Example 29 was repeated using 15% IPBC and 85% Matrix 3BM producing similar results.

EXAMPLE 31

15 g of Permethrin was dissolved in a mixture containing 42.5 g Matrix IM and 42.5 g PEG 500. This composition on dilution in water at 1/10, 1/50, 1/100, and 1/1000 was optically clear when stored at room temperature for more than one month.

Accelerated storage at 50° C. for 14 days showed practically no reduction in the concentration of Permethrin from the initial 15% level determined via HPLC analysis of aliquot samples.

Similarly, diluted samples at 1/100 in water, containing 0.15% Permethrin showed practically no loss on storage at 50° C. for 14 days, via HPLC analysis.

The above aqueous dilution containing 0.15% Permethrin was successfully found to protect wood treated under water to be resistant to termite attack.

EXAMPLE 32

10 g IPBC was dissolved in a mixture containing 45 g Matrix 1M and 45 g PEG (polyethylene glycol) 400. This composition on dilution in water at 1/10, 1/50, 1/100, and 1/1000 was optically clear when stored at room temperature for more than one month.

EXAMPLE 33

Example 32 was repeated with 20% loading compared to 10% loading. Samples diluted in water were stable with slight opalescence at 1/10 dilution and clear at other dilutions.

EXAMPLE 34

Compositions of Examples 32 and 33 were diluted to contain 0.1% IPBC and were used to treat fresh cut wood for preservation against wood-rotting fungi (Basidiomycete) in a 'dip' application and found to protect the treated wood.

In summary, certain derivatized vegetable oils can be used as formulation matrices to deliver bioactive materials like biocides (IPBC), insecticide (Permethrin), disinfectant (metachloroxylenol), oils (Pine oil), cleaning/degreasing product (L limonine) and others. The formulation medium can be made robust with increased loading of the bioactive materials, by combining with other formulation matrices with either co-solvents and/or emulsifiers, The following matrices are capable of producing nano-particular compositions in aqueous phase on dilution from a concentrate containing bio-active hydrophobic materials.

A combination of derivatized vegetable oil like: 2B, Maleated Linseed oil, neutralized with AMP (amino methyl propanol) and Matrix at 1:1 weight ratio, is capable of loading much higher amounts of active ingredients compared to the components [1M and 2B]. The higher-loaded concentrates on dilution produced stable nano-particular aqueous compositions.

Description of Modified Vegetable Oil (Neutralized with AMP to ~pH 7 at 1/10 Dilution)

Modified Vegetable Oil:

Vegetable oil is derivatized to provide an ionizable functionality to provide a) high solubility for bioactive materials and on dilution in water to provide sufficient hydrophobic environment to include the active materials in water, and stabilizing outside group like the ionized or polar functionality pointing into water.

The base oil of the invention (a) is a hydrophobic oil, ester such as a glyceride oil containing at least two double bonds capable of reacting with an alpha-beta unsaturated carbonyl compound (containing at least one carboxylate or ionizable moiety) to form a stable adduct, (b) is a hydrophobic oil containing at least one reactive group like hydroxyl moiety. Examples of these oils are:

(a) naturally occurring linseed oil, glyceryl esters (mono-, di-, preferably tri-esters) like glyceryl linoleate of linolenate preferably in the conjugated form, phytyl linoleate, phytyl linolenate, (b) castor oil, which is a triglyceride of hydroxyl stearic acid.

Examples of alpha-beta unsaturated compounds are: partially esterified maleic acid, partially esterified cinnamic acid, crotonic acid and the like.

The esters of the unsaturated acids are prepared using the corresponding anhydrides like maleic anhydride.

Storage stability of the concentrate compositions containing water sensitive active ingredients like hydrolytically labile products like IPBC, Permethrin and others, can be enhanced by treating the concentrates with dehydrating agents or water-scavengers. $P_2O_5$, CaO, anhydrous salts, epoxidized vegetable oils, carbodiimides are some examples.

EXAMPLE 35

Preparation of Modified Linseed Oil 500 g of maleic acid anhydride are partially esterified with ethyl alcohol. The partial ester is mixed with 900 g of linseed oil and pressure-cooked for 3-4 hours at 160° C., while being constantly stirred, preferably in the presence of catalytic amount of iodine. Any additional acid groups are neutralized up to pH with aminomethylpropanol. A suitable weight ratio of 1M/2B is between 0.1/1 and 1/0.1; a preferred range was 0.5/0.5.

What is claimed is:

1. A synergistic matrix composite comprising, a first matrix composition including:

(a) 12.5 g N-octylpyrrolidone, (b) optionally, 5-60% an organic solvent which is soluble in (a), (c) 74.5 g castor oil ethoxylate, (d) 11.0 g EO/PO (PEG oil L 31) copolymer, and (e) 2.0 g branched ethoxylated phosphate ester; and a second matrix composition comprising a polar polymeric material and maleated linseed oil; in a weight ratio of 1:1.

2. A composite according to claim 1 wherein said composite comprises a neutralized maleated linseed oil.

3. A composite according to claim 1 wherein (b) is present.

4. A concentrate including the composite of claim 1 and including one or more dissolved hydrophobic active ingredients, which upon dilution in water can provide a nano-particular distribution.

5. A concentrate according to claim 4, wherein the active ingredient is a biocide or mixtures thereof.

6. A formulation including the composite of claim 4 in an aqueous media.

7. A formulation including the concentrate of claim 5 in an aqueous media.

8. A formulation according to claim 6 which is a shampoo, paint, coating, detergent or hard surface cleaner formulation.

9. A composite according to claim 4 which exhibits a sustained release of said active.

10. A composite according to claim 1 wherein said composite comprises a polar polymeric compound.

11. A composite according to claim 10 wherein the polar polymeric compound comprises polyethylene glycol.

* * * * *